United States Patent
Agbuga

(10) Patent No.: US 10,481,097 B1
(45) Date of Patent: Nov. 19, 2019

(54) METHOD AND SYSTEM FOR DETECTING INCLUSIONS IN FLOAT GLASS BASED ON SPECTRAL REFLECTANCE ANALYSIS

(71) Applicant: Guardian Glass, LLC, Auburn Hills, MI (US)

(72) Inventor: Okan Agbuga, Berlin (DE)

(73) Assignee: GUARDIAN GLASS, LLC, Auburn Hills, MI (US)

( * ) Notice: Subject to any disclaimer, the term of this patent is extended or adjusted under 35 U.S.C. 154(b) by 0 days.

(21) Appl. No.: 16/148,057

(22) Filed: Oct. 1, 2018

(51) Int. Cl.
| | |
|---|---|
| *G01N 21/552* | (2014.01) |
| *G01N 21/65* | (2006.01) |
| *C03B 18/18* | (2006.01) |
| *C03C 3/087* | (2006.01) |
| *C03C 4/08* | (2006.01) |
| *C03C 4/02* | (2006.01) |

(52) U.S. Cl.
CPC ........... *G01N 21/658* (2013.01); *C03B 18/18* (2013.01); *C03C 3/087* (2013.01); *C03C 4/02* (2013.01); *C03C 4/082* (2013.01); *C03C 4/085* (2013.01); *G01N 21/552* (2013.01)

(58) Field of Classification Search
CPC ........... C03C 3/087; C03C 4/02; C03C 4/082; C03C 4/085; G01N 21/59
See application file for complete search history.

(56) References Cited

U.S. PATENT DOCUMENTS

| | | |
|---|---|---|
| 3,083,551 A | 4/1963 | Pilkington |
| 3,954,432 A | 5/1976 | Hummel et al. |
| 5,214,008 A | 5/1993 | Beckwith et al. |
| 7,511,807 B2 | 3/2009 | Fang et al. |
| 9,016,094 B2 | 4/2015 | Siess et al. |
| 2010/0182666 A1* | 7/2010 | Herbert .............. G02B 27/2214 359/200.7 |
| 2016/0102010 A1* | 4/2016 | Beall ....................... C03B 32/02 428/410 |

* cited by examiner

*Primary Examiner* — David P Porta
*Assistant Examiner* — Fani Boosalis

(57) ABSTRACT

A method and/or system is provided for detecting and/or identifying inclusions (e.g., nickel sulfide based inclusions/defects) in glass such as soda-lime-silica based float glass. In certain example instances, during and/or after the glass-making process, following the stage in the float process where the glass sheet is formed and floated on a molten material (e.g., tin bath) and cooled or allowed to cool such as via an annealing lehr, energy such as infrared (IR) energy is directed at the resulting glass and reflectance at various wavelengths is analyzed to detect inclusions.

27 Claims, 2 Drawing Sheets

METHOD AND SYSTEM FOR DETECTING INCLUSIONS IN FLOAT GLASS BASED ON SPECTRAL REFLECTANCE ANALYSIS

Example embodiments of this invention relate to a method and/or system for detecting inclusions and/or other defects (e.g., micro inclusions such as nickel sulfide based inclusions/defects, chrome based inclusions/defects, iron based inclusions/defects, metallic Si based inclusions/defects, etc.) in soda-lime-silica based glass, such as float glass. In certain example embodiments of this invention, energy (e.g., infrared (IR) and/or visible) may be directed from at least one light source toward the glass, and different wavelengths of reflected energy from the at least one light source are analyzed and compared and inclusions can be detected based on detected spectral reflectances at various wavelengths. The system may use a broad range spectral signals across a range of wavelengths, and the multispectral imaging based inclusion/defect detection system may identify and/or differentiate between different types of inclusions/defects by capturing and analyzing their respective spectral reflectance curves and differentiating therebetween.

BACKGROUND OF THE INVENTION

The process of making float glass is known in the art. For example, see U.S. Pat. Nos. 3,954,432, 3,083,551, 3,220,816, 7,743,630, 8,677,782, 9,016,094, and 5,214,008, the disclosures of all of which are hereby incorporated herein in their entireties by reference. Generally speaking, in a float glass-making line, batch materials are heated in a furnace or melter to form a glass melt. The glass melt is poured onto a bath of molten material such as tin (tin bath) and is then continuously cooled to form a float glass ribbon. The float glass ribbon is then forwarded to an annealing lehr for further processing and then may be cut to form solid glass articles, such as flat glass sheets. For float glass, the glass batch often includes soda, lime and silica to form soda-lime-silica based flat glass.

Float glass is widely used for windows in commercial and residential buildings, glass furniture, shower doors, and automotive windshields. For many products, float glass must be thermally tempered (undergo heating to at least 580 degrees C., followed by a rapid cooling) to ensure safety in case of breakage. Impurities from raw materials, sulfur from additive(s), and/or contaminations from the float process occasionally and unpredictably form unwanted chemical compounds (e.g., inclusions) during glass formation, which are undesirable defects in the glass. Nickel, for example, is known to spontaneously bond with sulfur to form inclusions of or based on nickel sulfide (of any suitable stoichiometry such as NiS).

Although typically harmless in annealed glass (e.g., made via the float process without any additional heat treatment such as thermal tempering), NiS inclusions are known for causing spontaneous breakage of thermally tempered glass. Moreover, NiS inclusions/defects in thermally tempered glass have caused catastrophic glass failure over long periods of time in installed products. Rejecting defective annealed glass, therefore, serves at least two purposes: a) increase production yield during the expensive thermal tempering and heat soaking stages, and b) minimize catastrophic failures of glass in installed products.

Nickel sulfide exists in different phases at different temperatures. For instance, two specific phases of NiS known are the alpha-phase and the beta-phase. At temperatures below 715 degrees F. (379 C), nickel sulfide is relatively stable in the beta-phase form. Above this temperature, it is stable in the alpha-phase. Therefore, when glass is produced in a furnace, it is likely that any NiS inclusions will be in the alpha-phase. In typical annealed glass, the slow cooling process provided by the annealing lehr allows the NiS ample time to transform to its beta-phase as the glass cools. However, in the fast cooling process used in both heat-strengthened and tempered glass, there is often insufficient time to complete the phase transition (which is a relatively slow process). The NiS inclusions are therefore trapped in the glass in their high-temperature alpha-phase. However, once the glass cools past the phase change temperature, the NiS inclusion seeks to reenter the lower energy beta-phase. For trapped inclusions, this process takes anywhere from months to years. This may have no effect on glass, were it not for the point that when the NiS changes from alpha-phase to beta-phase, it increases in volume such as by 2-4%. This expansion may create localized tensile stresses which can lead to glass failures.

Nickel sulfide is a compound that comes in various forms as well. The most common forms of nickel sulfide are $Ni_7S_6$, NiS, $NiS_{1.03}$, $Ni_3S_2$ and $Ni_3S_2$+Ni. When viewed under an electron microscope, $Ni_7S_6$, NiS, and $NiS_{1.03}$ are yellow-gold in color and have a rugged surface similar to a golf ball. These three types are non-magnetic and have been found to cause failure in tempered glass. Other types of inclusions (defects) also occur in glass.

Various methods have been used for inline detection of NiS inclusions and other micro-defects of similar size scale (e.g., 40-150 microns sized defects). U.S. Pat. No. 7,511,807, incorporated herein by reference, for example directs light at the glass and looks for light scattering in order to detect inclusions. Conventional techniques for detecting inclusions therefore have been inefficient and sometimes ineffective.

Conventional glass defect inspection solutions use 2D or 3D machine vision technique in the visible wavelength range. The conventional machine vision systems detect and categorize inclusion defects by shapes and intensities of images. Inclusions like NiS, metallic Si and even bubbles could be viewed as the same type of defects due to their similar shapes and intensities. The conventional machine vision systems are not designed and not capable to accurately detect NiS inclusions, and cannot reasonably differentiate NiS inclusions from other types of inclusions.

In view of the above, it will be apparent that there exists a need in the art for an improved method of making glass, and controlling glass quality, including an improved method and/or apparatus for detecting inclusions in soda-lime-silica based glass and/or in other types of glass.

SUMMARY OF EXAMPLE EMBODIMENTS OF THE INVENTION

A method and/or system is provided for detecting inclusions (e.g., nickel sulfide based inclusions/defects) in glass such as soda-lime-silica based glass. Inline systems and/or methods discussed herein may be used to detect, for example, inclusions/defects in glass such as float glass. For instance, methods and/or systems may be used to detect nickel sulfide inclusions and/or other micro-defects having a size of from about 30-300 μm, more preferably from about 40-200 μm, and/or may be used to differentiate such nickel sulfide based inclusions from both inclusion-free glass and from other inclusions.

In certain example embodiments, the soda-lime-silica based glass comprises a base glass portion that includes, by weight percentage: $SiO_2$ 67-75%, $Na_2O$ 10-20%, CaO 5-15%, $Al_2O_3$ 0-7%, MgO 0-7%, and $K_2O$ 0-7%. Optionally, a colorant portion of the glass may further include one or more colorants such as iron, selenium, cobalt, erbium and/or the like.

Example embodiments of this invention relate to a method and/or system for detecting inclusions and/or other defects (e.g., micro inclusions such as nickel sulfide based inclusions/defects, chrome based inclusions/defects, iron based inclusions/defects, metallic Si based inclusions/defects, etc.) in soda-lime-silica based glass, such as float glass. In certain example embodiments of this invention, energy (e.g., infrared (IR) and/or visible) may be directed from at least one light source toward the glass, and different wavelengths of reflected energy from the at least one light source are analyzed and compared and inclusions can be detected based on detected spectral reflectances at different wavelengths. The system may use a broad range of spectral signals across a range of wavelengths (e.g., from 500-2,500 nm, or from 800-2,000 nm, or from 900-1,700 nm, or from 950-1,250 nm, or particular wavelengths in any of these ranges), and the multispectral imaging based inclusion/defect detection system may identify and/or differentiate between different types of inclusions/defects by capturing and analyzing their respective spectral reflectance curves and differentiating therebetween. For example, nickel sulfide inclusions/defects will affect a given wavelength range (e.g., 950-1250 nm, and/or particular wavelengths in that range) differently than will inclusion-free glass and differently than will other types of inclusions such as chrome based inclusions/defects and iron based inclusions/defects. Thus, for example, nickel sulfide based inclusions may be detected and identified based on at least analysis of reflectance by such nickel sulfide based inclusions at different wavelengths, whereas float glass itself absent inclusions and other types of inclusions/defects have different effects on reflectance at those wavelengths and thus can be differentiated from the nickel sulfide based inclusions.

This detection system may be implemented during and/or after the glass-making process, such as following the stage in the float process where the glass sheet is formed and floated on a molten material (e.g., tin bath) and cooled or allowed to at least partially cool such as after an annealing lehr. Energy from at least one light source(s) may be directed at the resulting glass and inclusions may be detected based on analyzing and/or comparing reflected energy as a function of wavelength ($\lambda$).

In an example embodiment of this invention, there is provided a method of detecting an inclusion in glass, the glass including a base glass composition comprising, by weight %, $SiO_2$ 67-75%, CaO 5-15%, $Al_2O_3$ 0-7%, and $K_2O$ 0-7%, the method comprising: directing energy from at least one source toward the glass; and determining whether an inclusion is present in the glass based on at least an analysis of reflectance values from the glass at different wavelengths. The at least one source may emit energy comprising infrared (IR) energy toward the glass, and said determining whether an inclusion is present in the glass may be based on at least an analysis of reflectance values from the glass at different IR wavelengths.

In an example embodiment of this invention, there is provided a method of detecting an inclusion in glass, the method comprising: directing energy from at least one source toward the glass; and determining whether an inclusion is present in the glass based on at least an analysis of reflectance and/or luminescence values from the glass at various wavelengths. The at least one source may emit energy comprising infrared (IR) energy toward the glass, and said determining whether an inclusion is present in the glass may be based on at least an analysis of reflectance and/or luminescence values from the glass at various IR wavelengths. Said determining whether an inclusion is present in the glass may be based on at least an analysis of reflectance and/or luminescence values from the glass at various IR wavelengths within a range from 800-2,000 nm, and/or within a range from 900-1,700 nm. The source(s) may optionally be located at least below the glass, and an imaging camera receiving IR from the glass may be located above the glass, so that the glass may be located between the source and the camera.

DETAILED DESCRIPTION OF EXAMPLE EMBODIMENTS OF THIS INVENTION

Figure 1:
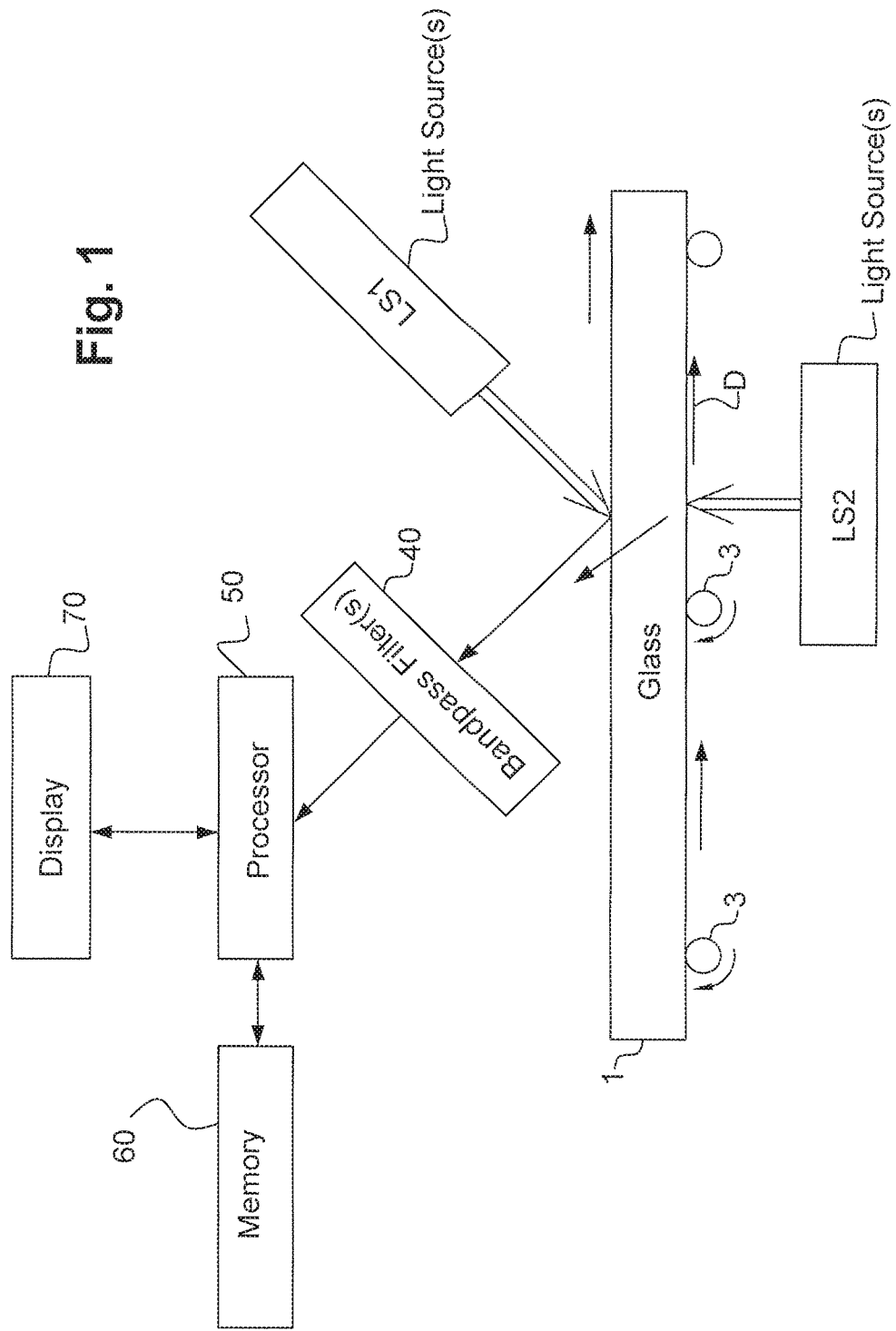
FIG. 1 is a diagram of a system for detecting inclusions in float glass according to an example embodiment of this invention.

A method and/or system is provided for detecting inclusions in glass such as soda-lime-silica based glass 1. For example, methods and/or systems may be used to detect nickel sulfide inclusions and/or other micro-defects having a size of from about 30-300 μm, more preferably from about 40-200 μm, and/or may be used to differentiate such nickel sulfide based inclusions from both inclusion-free glass and from other types of inclusions of these sizes or other sizes. In certain example embodiments, the soda-lime-silica based glass 1 comprises a base glass portion that includes, by weight percentage: $SiO_2$ 67-75%, $Na_2O$ 10-20%, CaO 5-15%, $Al_2O_3$ 0-7%, MgO 0-7%, and $K_2O$ 0-7%. Optionally, a colorant portion of the glass may further include one or more colorants such as iron, selenium, cobalt, erbium and/or the like. Alternatively, the glass 1 may be a different type of glass such as borosilicate glass, aluminosilicate glass, or the like.

An example soda-lime-silica base glass 1 according to certain example embodiments of this invention that may be made via the float process or other suitable process, on a weight percentage basis, includes the following basic ingredients:

TABLE 1

| Example Base Glass | |
| --- | --- |
| Ingredient | Wt. % |
| $SiO_2$ | 67-75% |
| $Na_2O$ | 10-20% |
| CaO | 5-15% |
| MgO | 0-7% |
| $Al_2O_3$ | 0-7% |
| $K_2O$ | 0-7% |

Other minor ingredients, including various refining aids, such as salt cake, crystalline water and/or the like may also be included in the base glass. In certain embodiments, for example, glass 1 herein may be made from batch raw materials silica sand, soda ash, dolomite, limestone, with the use of salt cake (SO$_3$) as a refining agent. Reducing and oxidizing agent(s) may also be used in certain instances. In certain instances, soda-lime-silica base glasses 1 herein may include by weight from about 10-15% Na$_2$O and from about 6-12% CaO. In addition to the base glass materials discussed above, the glass batch and/or final glass 1 may also include a colorant portion including material(s) such as iron, erbium, cobalt, selenium and/or the like in suitable amounts in order to provide coloration and/or absorption to the glass in a desired manner. In certain example embodiments of this invention, the amount of total iron in the glass may be from about 0.05 to 1.2%, more preferably from about 0.3 to 0.8%. In the case of certain clear high transmission glasses, the total iron may be from about 0.005 to 0.025%. The total amount of iron present in the glass, and thus in the colorant portion thereof, is expressed herein in terms of Fe$_2$O$_3$ in accordance with standard practice. This, however, does not imply that all iron is actually in the form of Fe$_2$O$_3$. Likewise, the amount of iron in the ferrous state is reported herein as FeO, even though all ferrous state iron in the glass may not be in the form of FeO.

When making the glass via the float process for example, the glass batch raw materials (e.g., silica sand, soda ash, dolomite, limestone, colorant(s), etc.) are provided in and heated in a furnace or melter to form a glass melt. The glass melt is poured onto a bath of molten material such as tin (tin bath), where the glass is formed and continuously cooled to form a float glass ribbon. The float glass ribbon proceeds toward an annealing lehr for slow cooling. Optionally, prior to entering the annealing lehr, lateral edge portion(s) of the glass sheet may be trimmed in a hot condition. The glass sheet typically reaches the beginning of the annealing lehr at a temperature of at least about 540 degrees C., more preferably at least about 580 degrees, C, with a possible range from about 540 (or 580) to 800 degrees C. During the annealing, the temperature of the glass sheet strip is slowly cooled from the annealing point (e.g., from about 538-560 degrees C.) to a strain point of from about 495-560 degrees C., which may be referred to as an annealing range. While these temperature ranges are preferred for annealing, different temperatures may be used in certain instances. The continuous glass sheet may be supported by either rollers or gas during annealing. After annealing, the continuous glass sheet is moved on for further processing such as one or more of cutting, additional cooling, coating and/or the like.

As explained above, impurities from raw materials, sulfur from additive(s), and/or contaminations from the float process, occasionally and unpredictably form unwanted chemical compounds (e.g., inclusions) during glass formation, which are undesirable defects in the glass. Nickel, for example, is known to spontaneously bond with sulfur to form inclusions of or based on nickel sulfide (of any suitable stoichiometry such as NiS).

Figure 2:
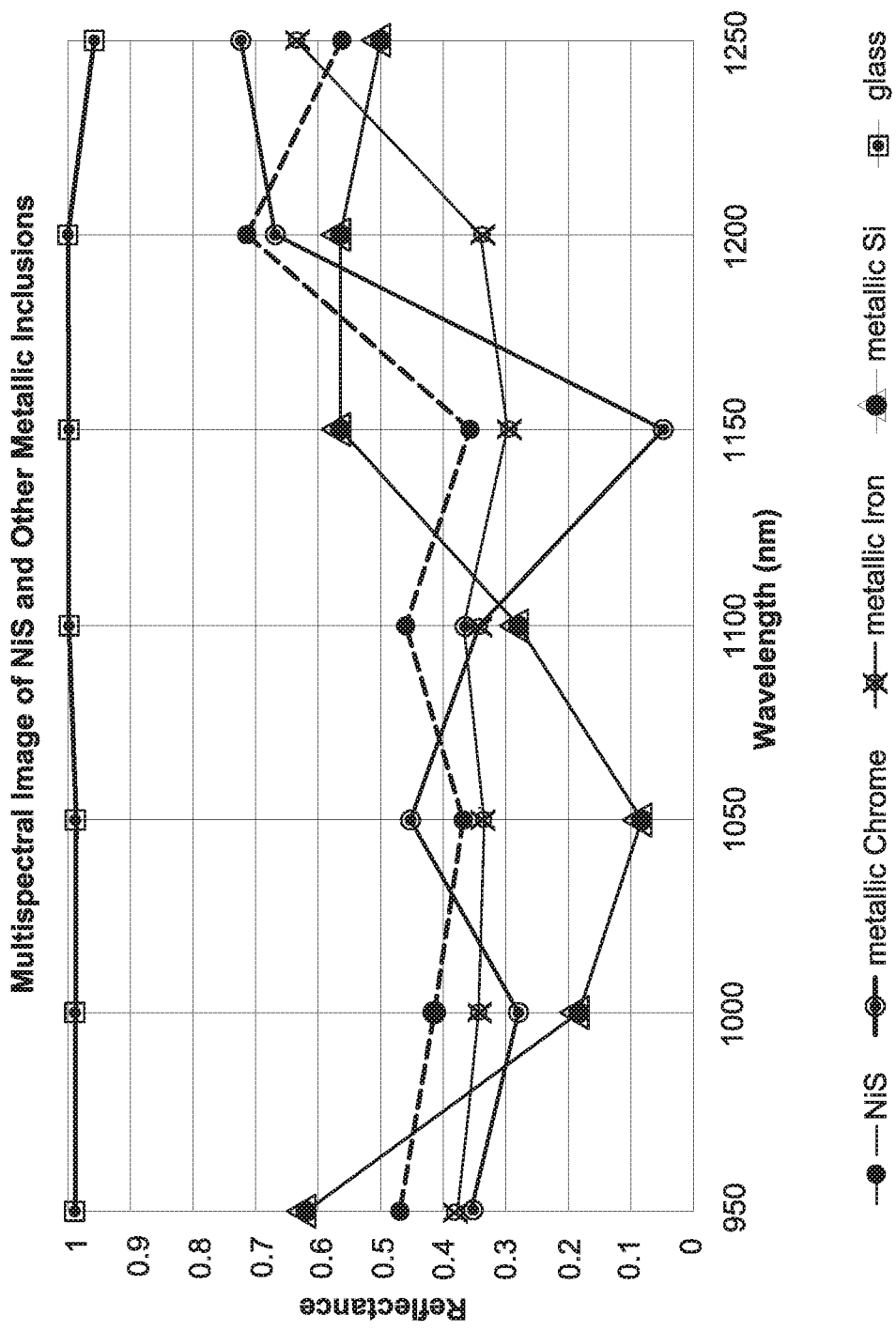
FIG. 2 is a reflectance vs. wavelength (nm) graph illustrating that inclusion-free glass, and different inclusions such as nickel sulfide based inclusions, chrome based inclusions, iron based inclusions, and metallic silicon based inclusions, have different spectral reflectance characteristics as a function of wavelength, across a range of wavelengths.

In reflected-light spectroscopy, a fundamental property involved herein is spectral reflectance and luminescence (or simply called "spectral reflectance"). Spectral reflectance and luminescence (or "spectral reflectance") is the ratio of reflected energy to incident energy as a function of wavelength. Spectral reflectance varies with wavelength for different types of materials. Wavelength-specific reflectance of a material can be caused by spectral absorption of the particular chemical elements or ions, the ionic charge of certain elements, and/or the geometry of chemical bonds between elements for example. For example, inclusion-free soda-lime-silica based glass, nickel sulfide based inclusions, chrome based inclusions, iron based inclusions, and metallic Si based inclusions each have different respective spectral reflectance curves, such as what is shown in FIG. 2 over a particular range of wavelengths. As another example provided for purposes of understanding, Kaolinite and montmorillonite are clay minerals that are common in soils, and the strong absorption band near 1.4 μm in both spectra, along with the weak 1.9 μm band in kaolinite, are due to hydroxide ions (OH-1), while the stronger 1.9 μm band in montmorillonite is caused by bound water molecules in this hydrous clay.

In example embodiments of this invention, stored spectral curves in memory 60 for different types of materials, and/or absorption bands (location and strength), may be used by processor 50 to identify and discriminate different materials (e.g., nickel sulfide based inclusions, chrome based inclusions, etc.) thereby allowing inclusions to be detected and identified in glass 1 such as soda-lime-silica based glass. In certain example embodiments of this invention, multispectral imaging technology may use a broad range of spectral signals (e.g., from visible to IR, or just in IR) and the multispectral imaging based defect detection system identifies different types of inclusion defects in glass 1 by capturing their spectral reflectance curve difference (or values, or value differences) and analyzing same such as against stored curves (or values) for different materials. An extended artificial intelligence (AI) multispectral imaging approach may be used in certain example embodiments, with stored curves for different types of materials (e.g., different types of inclusions) being learned over time.

FIG. 1 illustrates an example system for detecting inclusions/defects in glass such as soda-lime-silica based glass 1 moving in direction D on rollers 3. Energy (e.g., shortwave IR, IR, visible, and/or any combination thereof) from at least one energy/light source LS1 and/or LS2 is directed at the glass 1. The light from the source(s) LS1 and/or LS2 may or may not be focused on the glass 1, such as being focused on the upper and/or lower surface of the glass. In certain example embodiments, only energy/light source(s) above the glass 1 may be used such as shown by LS1 in FIG. 1. However, in certain example embodiments (such as embodiments where the spectral curves in FIG. 2 were obtained), only energy/light source(s) below the glass 1 may be used such as shown by LS2 in FIG. 1. The glass, and any inclusions therein, reflect this energy (from LS1 and/or LS2) as a function of wavelength toward bandpass filters 40 as shown in FIG. 1. As explained here, each material has a different reflectance characteristic. For example, a multispectral image may captures reflectance from the glass 1 over 3-7 spectral bands through bandpass filters 40. Inclusions in the glass may then be detected by the processor 50, by comparing received reflectance spectra from the glass 1 against prior determined spectral curves and/or values for various materials (e.g., for the types of inclusions and inclusion free glass discussed herein) in memory 60. In certain example embodiments, the multispectral imaging system may include selections of bandpass filters 40 for allowing the processor to find/identify/determine the spectral reflectance ("fingerprint") for NiS or any other inclusion(s) over suitable wavelength range such as over 900-1700 nm. It has been found, and shown in FIG. 2, that NiS inclusions have clearly different spectral reflectance curve(s) compared to other metallic inclusions. While other metallic inclusions (such as Si-Ball) and NiS inclusions have been found to have similar intensities in the visible range, they have been found to have very different reflectance values in near IR (NIR) range which is why ranges including 900-1700 nm have been found to be particularly advantageous in example embodiments of this invention. For example, the processor 50 can identify different respective spectral reflectances of NiS and other metallic inclusions with extended measurement technique using cooled SWIR InGaAs area-scanning camera(s) (e.g., 40 kHz InGaAs scanning cameras), IR illumination source(s) (e.g., LS1 and/or LS2), and specific OD4 filters between 950 nm and 1250 nm with 50 nm band-pass steps (which may or may not be integrated with the camera(s)), in example embodiments of this invention. Such camera(s) including an imaging device for receiving IR from the glass, and may or may not include elements 40-70 shown in FIG. 1. Results such as identification and location of detected inclusions may be stored in memory 60 and/or displayed on display 70 for an operator to view.

FIG. 2 illustrates the spectral reflectance characteristics of nickel sulfide based inclusions, chrome based inclusions, iron based inclusions, silicon based inclusions, and inclusion-free glass, over a wavelength range of from 950 to 1250 nm. IR light source was positioned below the glass, as shown by LS2 in FIG. 1, in order to obtain the spectral curves for the various inclusions and the glass in FIG. 2. For example, FIG. 2 illustrates that at 1000 nm silicon based inclusions have a reflectance of about 0.18, chrome based inclusions have a reflectance of about 0.29, iron based inclusions have a reflectance of about 0.33, nickel sulfide based inclusions have a reflectance of about 0.42, and inclusion-free glass has a reflectance of almost 1.0. As another example, FIG. 2 illustrates that at 1050 nm silicon based inclusions have a reflectance of about 0.08, chrome based inclusions have a reflectance of about 0.46, iron based inclusions have a reflectance of about 0.32, nickel sulfide based inclusions have a reflectance of about 0.38, and inclusion-free glass has a reflectance of almost 1.0. As another example, FIG. 2 illustrates that at 1150 nm silicon based inclusions have a reflectance of about 0.58, chrome based inclusions have a reflectance of about 0.06, iron based inclusions have a reflectance of about 0.30, nickel sulfide based inclusions have a reflectance of about 0.38, and inclusion-free glass has a reflectance of about 1.0. As another example, FIG. 2 illustrates that at 1200 nm silicon based inclusions have a reflectance of about 0.58, chrome based inclusions have a reflectance of about 0.68, iron based inclusions have a reflectance of about 0.32, nickel sulfide based inclusions have a reflectance of about 0.58, and inclusion-free glass has a reflectance of about 1.0. The respective spectral reflectance curves shown in FIG. 2 for various types of materials in glass may be obtain by sampling at any suitable rate, such as, for example and without limitation, every 50 nm and/or an integration time of 200 ms. Such curves and/or values may be stored in memory 60, so that processor 50 can compared received reflectance data from the glass 1 with such data stored in memory 60 in order to detect and identify inclusions such as nickel sulfide inclusions, and to differentiate different types of inclusions from each other. For example, it can be seen from FIG. 2 that processor 50 may detect each of silicon based inclusions, chrome based inclusions, iron based inclusions, and nickel sulfide based inclusions in the glass 1, and may differentiate the different types of inclusion from each other based on the stored and received spectral reflectance data.

Thus, example embodiments of this invention involve a method and/or system for detecting inclusions and/or other defects (e.g., micro inclusions such as nickel sulfide inclusions/defects, chrome based inclusions/defects, iron based inclusions/defects, metallic Si based inclusions/defects, etc.) in soda-lime-silica based glass, such as float glass. In certain example embodiments of this invention, energy (e.g., infrared (IR) and/or visible) may be directed from at least one light source toward the glass, and different wavelengths of reflected energy (e.g., refracted and/or scattered light) from the at least one light source are analyzed and compared and inclusions can be detected based on detected reflectances at different wavelengths. The system may use a broad range of spectral signals across a range of wavelengths (e.g., from 500-2,500 nm, or from 800-2,000 nm, or from 900-1,700 nm, or from 950-1,250 nm, or particular wavelengths in any of these ranges), and the multispectral imaging based inclusion/defect detection system may identify and/or differentiate between different types of inclusions/defects by capturing and analyzing their respective spectral reflectance curves and differentiating therebetween. For example, nickel sulfide inclusions/defects will affect a given wavelength range (e.g., 950-1250 nm, and/or particular wavelengths in that range) differently than will inclusion-free glass and differently than will other types of inclusions such as chrome based inclusions/defects and iron based inclusions/defects. Thus, for example, nickel sulfide based inclusions may be detected and identified based on at least analysis of reflectance by such nickel sulfide based inclusions at different wavelengths, whereas float glass itself absent inclusions and other types of inclusions/defects have different effects on reflectance at those wavelengths and thus can be differentiated from the nickel sulfide based inclusions.

In an example embodiment of this invention, during and/or after the glass-making process, following the stage in the float process where the glass sheet is formed and floated on a molten material (e.g., tin bath) and cooled or allowed to at least partially cool such as after an annealing lehr, the system shown in FIG. 1 may be provided. The system shown in FIG. 1 for detecting inclusions, such as nickel sulfide (of any stoichiometry) based inclusions, in the glass 1 may be located on the float line after the annealing lehr, and before or after a glass cutting station, in certain example embodiments of this invention. When inclusion(s) are found in the glass, that portion of the glass is discarded and/or not subjected to thermal tempering. Alternatively, the inclusion detecting system shown in FIG. 1 may instead be located separate from the float line, such as at a station between the float line and a tempering furnace, or at a station just prior to a tempering furnace in a tempering facility, in order to detect inclusions and discard glass with inclusions prior to thermal tempering. Such an inclusion detection process may also be utilized during or after manufacture of other types of glass such as borosilicate glass, aluminosilicate glass, or the like (as opposed to during or after just a float process for making soda-lime-silica based glass).

Glass made in this manner, after passing the detection station with no inclusions being detected, is useful, for example and without limitation, in glass window applications for buildings and/or vehicles, solar cell applications, furniture glass applications, and/or display glass applications.

In an example embodiment of this invention, there is provided a method of detecting an inclusion in glass, the glass including a base glass composition comprising, by weight %, $SiO_2$ 67-75%, CaO 5-15%, $Al_2O_3$ 0-7%, and $K_2O$ 0-7%, the method comprising: directing energy from at least one source toward the glass; and determining whether an inclusion is present in the glass based on at least an analysis of reflectance values from the glass at different wavelengths.

In the method of the immediately preceding paragraph, the at least one source may emit energy comprising infrared (IR) energy toward the glass, and said determining whether an inclusion is present in the glass may be based on at least an analysis of reflectance values from the glass at different IR wavelengths.

In the method of any of the preceding two paragraphs, said determining whether an inclusion is present in the glass may be based on at least an analysis of reflectance values from the glass at different IR wavelengths within a range of 800-2,000 nm, possibly within a range from 900-1,700 nm, and possibly within a range from 950-1,250 nm.

In the method of any of the preceding three paragraphs, at least one bandpass filter may be provided between the glass and a camera for receiving reflected energy from the glass.

In the method of any of the preceding four paragraphs, the inclusion may be of or include nickel sulfide.

The method of any of the preceding five paragraphs may further comprise identifying and differentiating between different inclusions of different materials in the glass based on at least an analysis of reflectance values from the glass at different wavelengths.

The method of any of the preceding six paragraphs may further comprise identifying and differentiating between nickel sulfide based inclusions and Cr based inclusions in the glass based on at least an analysis of reflectance values from the glass at different wavelengths.

The method of any of the preceding seven paragraphs may further comprise identifying and differentiating between nickel sulfide based inclusions and iron based inclusions in the glass based on at least an analysis of reflectance values from the glass at different wavelengths.

The method of any of the preceding eight paragraphs may further comprise determining whether to pass or reject the glass based at least on whether an inclusion is detected.

In the method of any of the preceding nine paragraphs, the source may be located on and/or in a float line, and may be positioned after an annealing lehr of the float line.

In an example embodiment of this invention, there is provided a method of detecting an inclusion in glass, the method comprising: directing energy from at least one source toward the glass; and determining whether an inclusion is present in the glass based on at least an analysis of reflectance and/or luminescence values from the glass at various wavelengths.

In the method of the immediately preceding paragraph, the at least one source may emit energy comprising infrared (IR) energy toward the glass, and said determining whether an inclusion is present in the glass may be based on at least an analysis of reflectance and/or luminescence values from the glass at various IR wavelengths.

In the method of any of the preceding two paragraphs, said determining whether an inclusion is present in the glass may be based on at least an analysis of reflectance and/or luminescence values from the glass at various IR wavelengths within a range from 800-2,000 nm.

In the method of any of the preceding three paragraphs, said determining whether an inclusion is present in the glass is based on at least an analysis of reflectance and/or luminescence values from the glass at various IR wavelengths within a range from 900-1,700 nm.

In the method of any of the preceding four paragraphs, the source(s) may located at least below the glass, and a camera receiving IR from the glass may be located above the glass, so that the glass may be located between the source and the camera.

Once given the above disclosure many other features, modifications and improvements will become apparent to the skilled artisan. Such features, modifications and improvements are therefore considered to be a part of this invention, the scope of which is to be determined by the following claims:

What is claimed is:

1. A method of detecting an inclusion in glass, the glass including a base glass composition comprising:

| Ingredient | wt. % |
| --- | --- |
| $SiO_2$ | 67-75% |
| $Na_2O$ | 10-20% |
| CaO | 5-15% |
| $Al_2O_3$ | 0-7% |
| $K_2O$ | 0-7% | the method comprising:
   directing energy from at least one source toward the glass; and
   determining whether an inclusion is present in the glass based on at least an analysis of reflectance values from the glass at different wavelengths.

2. The method of claim 1, wherein the at least one source emits energy comprising infrared (IR) energy toward the glass, and said determining whether an inclusion is present in the glass is based on at least an analysis of reflectance values from the glass at different IR wavelengths.

3. The method of claim 1, wherein said determining whether an inclusion is present in the glass is based on at least an analysis of reflectance values from the glass at different IR wavelengths within a range from 800-2,000 nm.

4. The method of claim 1, wherein said determining whether an inclusion is present in the glass is based on at least an analysis of reflectance values from the glass at different IR wavelengths within a range from 900-1,700 nm.

5. The method of claim 1, wherein said determining whether an inclusion is present in the glass is based on at least an analysis of reflectance values from the glass at different IR wavelengths within a range from 950-1,250 nm.

6. The method of claim 1, wherein at least one bandpass filter is provided between the glass and a camera for receiving reflected energy from the glass.

7. The method of claim 1, wherein the inclusion comprises nickel sulfide.

8. The method of claim 1, further comprising identifying and differentiating between different inclusions of different materials in the glass based on at least an analysis of reflectance values from the glass at different wavelengths.

9. The method of claim 1, further comprising identifying and differentiating between nickel sulfide based inclusions and Cr based inclusions in the glass based on at least an analysis of reflectance values from the glass at different wavelengths.

10. The method of claim 1, further comprising identifying and differentiating between nickel sulfide based inclusions and iron based inclusions in the glass based on at least an analysis of reflectance values from the glass at different wavelengths.

11. The method of claim 1, further comprising determining whether to pass or reject the glass based at least on whether an inclusion is detected.

12. The method of claim 1, wherein the source is located on and/or in a float line, and is positioned after an annealing lehr of the float line.

13. A method of detecting an inclusion in glass, the method comprising:
   directing energy from at least one source toward the glass which comprises a base glass composition comprising:

| Ingredient | wt. % |
| --- | --- |
| SiO$_2$ | 67-75% |
| Na$_2$O | 10-20% |
| CaO | 5-15% |
| Al$_2$O$_3$ | 0-7% |
| K$_2$O | 0-7%; and | determining whether an inclusion comprising nickel sulfide is present in the glass based on at least an analysis of reflectance values from the glass at different infrared (IR) wavelengths.

14. The method of claim 13, wherein said determining whether an inclusion is present in the glass is based on at least an analysis of reflectance values from the glass at different IR wavelengths within a range from 800-2,000 nm.

15. The method of claim 13, further comprising identifying and differentiating between different inclusions of different materials in the glass based on at least an analysis of reflectance values from the glass at different IR wavelengths.

16. A system for detecting an inclusion in glass, the glass including a base glass composition comprising:

| Ingredient | wt. % |
| --- | --- |
| SiO$_2$ | 67-75% |
| Na$_2$O | 10-20% |
| CaO | 5-15% |
| Al$_2$O$_3$ | 0-7% |
| K$_2$O | 0-7% | the system comprising:
  at least one source for directing energy toward the glass; and
  a processor configured to determine whether an inclusion is present in the glass based on at least an analysis of spectral reflectance and/or luminescence values from the glass at different wavelengths.

17. The system of claim 16, wherein the at least one source is configured to emit energy comprising infrared (IR) energy toward the glass, and said processor is configured to determine whether an inclusion is present in the glass based on at least an analysis of spectral reflectance and/or luminescence values from the glass at different IR wavelengths.

18. The system of claim 16, wherein the processor is configured to determine whether an inclusion is present in the glass based on at least an analysis of spectral reflectance and/or luminescence values from the glass at different IR wavelengths within a range from 800-2,000 nm.

19. The system of claim 16, wherein the processor is configured to determine whether an inclusion is present in the glass based on at least an analysis of spectral reflectance and/or luminescence values from the glass at different IR wavelengths within a range from 900-1,700 nm.

20. The system of claim 16, wherein at least one bandpass filter is provided between the glass and a camera for receiving reflected energy from the glass.

21. The system of claim 16, wherein the inclusion comprises nickel sulfide.

22. The system of claim 16, wherein the processor is further configured to identify and differentiate between different inclusions of different materials in the glass based on at least an analysis of spectral reflectance and/or luminescence values from the glass at different wavelengths.

23. A method of detecting an inclusion in glass, the method comprising:
  directing energy from at least one source toward the glass which comprises a base glass composition comprising:

| Ingredient | wt. % |
| --- | --- |
| SiO$_2$ | 67-75% |
| Na$_2$O | 10-20% |
| CaO | 5-15% |
| Al$_2$O$_3$ | 0-7% |
| K$_2$O | 0-7%; and | determining whether an inclusion is present in the glass based on at least an analysis of reflectance and/or luminescence values from the glass at various wavelengths.

24. The method of claim 23, wherein the at least one source emits energy comprising infrared (IR) energy toward the glass, and said determining whether an inclusion is present in the glass is based on at least an analysis of reflectance and/or luminescence values from the glass at various IR wavelengths.

25. The method of claim 23, wherein said determining whether an inclusion is present in the glass is based on at least an analysis of reflectance and/or luminescence values from the glass at various IR wavelengths within a range from 800-2,000 nm.

26. The method of claim 23, wherein said determining whether an inclusion is present in the glass is based on at least an analysis of reflectance and/or luminescence values from the glass at various IR wavelengths within a range from 900-1,700 nm.

27. The method of claim 23, wherein the source is located below the glass, and a camera receiving IR from the glass is located above the glass, so that the glass is located between the source and the camera.

* * * * *